US009351693B2

(12) United States Patent
Sharpless et al.

(10) Patent No.: US 9,351,693 B2
(45) Date of Patent: May 31, 2016

(54) IMAGING SYSTEM GANTRY TILT SUPPORT (75) Inventors: Ronald B. Sharpless, Cleveland, OH (US); Johannes Balthasar Maria Soetens, Esbeek (NL)

(73) Assignee: KONLIJKE PHILIPS N.V., Eindhoven (NL)

( * ) Notice: Subject to any disclaimer, the term of this patent is extended or adjusted under 35 U.S.C. 154(b) by 80 days.

(21) Appl. No.: 14/237,020

(22) PCT Filed: Aug. 2, 2012

(86) PCT No.: PCT/IB2012/053952
§ 371 (c)(1),
(2), (4) Date: Feb. 4, 2014

(87) PCT Pub. No.: WO2013/021319
PCT Pub. Date: Feb. 14, 2013

(65) Prior Publication Data
US 2014/0205059 A1   Jul. 24, 2014

Related U.S. Application Data (60) Provisional application No. 61/521,777, filed on Aug. 10, 2011.

(51) Int. Cl.
*A61B 6/03*   (2006.01)
*H05G 1/02*   (2006.01)
*A61B 6/00*   (2006.01)

(52) U.S. Cl.
CPC .............. *A61B 6/4447* (2013.01); *A61B 6/035* (2013.01); *A61B 6/4429* (2013.01); *A61B 6/4435* (2013.01); *A61B 6/44* (2013.01)

(58) Field of Classification Search
CPC ............. A61N 5/00; A61N 5/01; A61N 5/10; A61N 2005/0632; A61N 2005/0633; A61B 6/00; A61B 6/02; A61B 6/025; A61B 6/03; A61B 6/032; A61B 6/035; A61B 6/04; A61B 6/40; A61B 6/44; A61B 6/4411; A61B 6/4429; A61B 6/4435; A61B 6/4447; H05G 1/00; H05G 1/02; F16F 1/00; F16F 1/02; F16F 1/025; F16F 1/027; F16F 1/18; F16F 1/182; F16F 1/26; F16F 1/28; F16F 1/368; F16F 1/3686; F16F 3/00; F16F 3/02; F16F 3/023
USPC .............. 378/4–20, 189, 193–198, 204, 205, 378/210; 600/407, 425, 426
See application file for complete search history.

(56) References Cited

U.S. PATENT DOCUMENTS 4,115,695 A * 9/1978 Kelman ........................ 378/17
4,750,195 A   6/1988 Takahashi
(Continued)

FOREIGN PATENT DOCUMENTS

JP   2011104118 A   6/2011
WO  2010052623 A1   5/2010

*Primary Examiner* — Anastasia Midkiff (57) ABSTRACT

An imaging system (500) includes an annular shaped rotating gantry (504) having an aperture (501) and configured to support at least a radiation source, wherein the rotating gantry rotates about a rotation axis (508) around an examination region, and wherein the rotation axis is located within the aperture in a center region (508) of the examination region. The imaging system further includes a stationary gantry (502), configured to rotatably support the rotating gantry. The stationary gantry includes a gantry base (516), an annular shaped tilt frame (518) that rotatably supports the rotating gantry, and a tilt system (520) affixed to and between the gantry base and the tilt frame, wherein the tilt system defines a tilt axis (522) of the stationary gantry, the tilt axis is located between the gantry base and the rotation axis, and the tilt frame tilts about the tilt axis.

23 Claims, 12 Drawing Sheets

(56) References Cited

U.S. PATENT DOCUMENTS

| | | |
|---|---|---|
| 4,928,292 A | 5/1990 | Zupancic et al. |
| 5,703,921 A | 12/1997 | Fujita et al. |
| 6,289,073 B1 * | 9/2001 | Sasaki et al. .................. 378/4 |
| 6,452,998 B2 | 9/2002 | Tybinkowski et al. |
| 2005/0133975 A1 * | 6/2005 | Rousseau .................. 267/36.1 |
| 2008/0025460 A1 * | 1/2008 | Li .................. 378/15 |
| 2010/0142669 A1 | 6/2010 | Ren et al. |
| 2010/0214675 A1 * | 8/2010 | Kugler et al. .................. 359/811 |

* cited by examiner

IMAGING SYSTEM GANTRY TILT SUPPORT

CROSS REFERENCE TO RELATED APPLICATIONS

This application is a national filing of PCT application Ser. No. PCT/IB2012/053952, filed Aug. 2, 2012, published as WO 2013/021319 A2 on Feb. 14, 2013, which claims the benefit of U.S. provisional application Ser. No. 61/521,777 filed Aug. 10, 2011, which is incorporated herein by reference.

FIELD OF THE INVENTION

The following generally relates to an imaging system and is described with particular application to computed tomography (CT). However, it is to be appreciated that the following is also amenable to other imaging modalities.

BACKGROUND OF THE INVENTION

Figure 1:
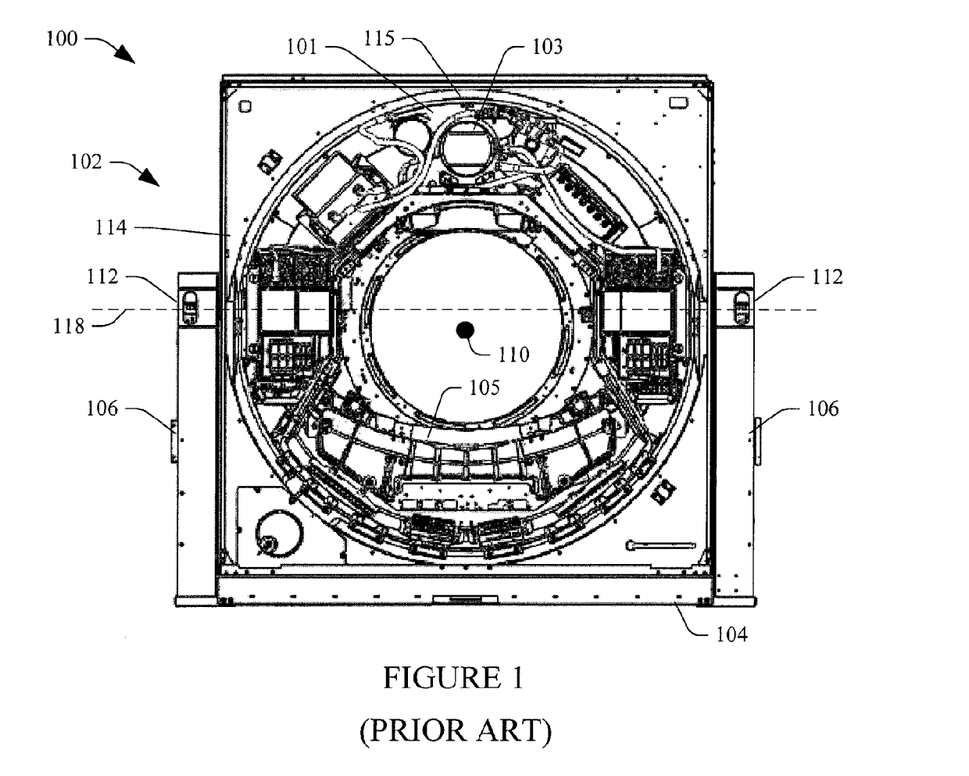
FIGS. 1, 2, 3 and 4 illustrate an example prior art tilt support for an imaging system.
Figure 2:
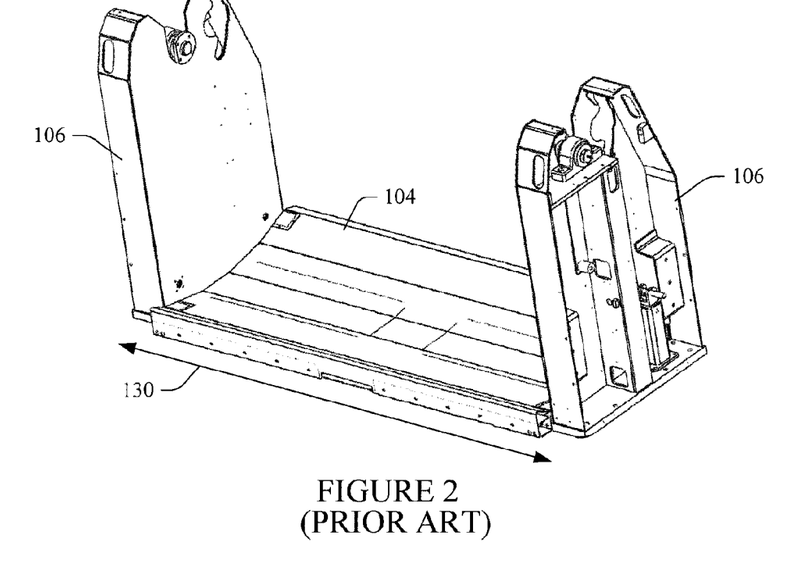
Figure 3:
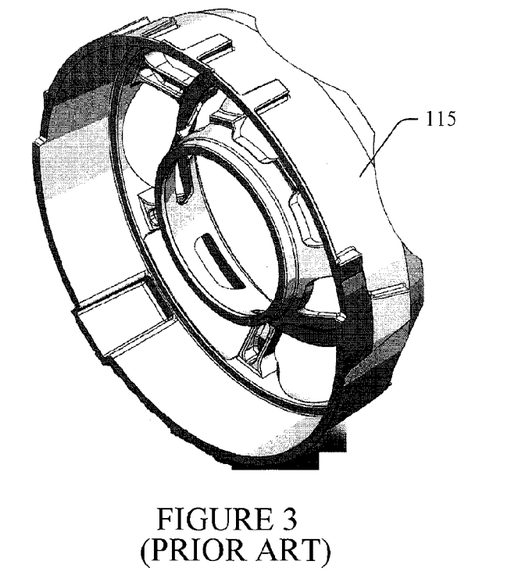

With reference to FIG. 1, a conventional computed tomography (CT) scanner 100 generally includes a rotating gantry 101 rotatably supported by a stationary gantry 102. The rotating gantry 101 supports at least an x-ray tube 103, which emits radiation that traverses an examination region and a portion of an object or subject therein. A subject support 120 (FIG. 4) supports a subject or object in the examination region. The illustrated rotating gantry 101 also supports a detector array 105, which is located opposite the radiation source 103 across the examination region, and which detects radiation traversing the examination region. The detector array 105 generates a signal, which is reconstructed to generate volumetric image data. Scans are performed with the rotating gantry in a vertical non-tilted position (FIG. 1) or a tilted position.

As shown in FIGS. 1, 2, 3 and 4, with the illustrated CT scanner 100, the stationary gantry 102 includes a gantry base 104 (FIGS. 1, 2 and 4), which mounts (e.g., via four (4) to six (6) or other number of different points over the area of the base 104) to the examination room floor, side supports 106 (FIGS. 1, 2 and 4), which extend vertically upward from the gantry base 104 to a height near the center 110 of the examination region (FIG. 1), a tilt support 112 (FIGS. 1 and 4), such as ball or other bearings, which are located in the side supports 106 up at a height near the center 110 of the examination region such as at a center of gravity of the system (FIG. 1), and a tilt frame 114 (FIGS. 1 and 4), which includes a support frame 115 (FIGS. 1 and 3), which rotatably supports the rotating gantry 101.

Figure 4:
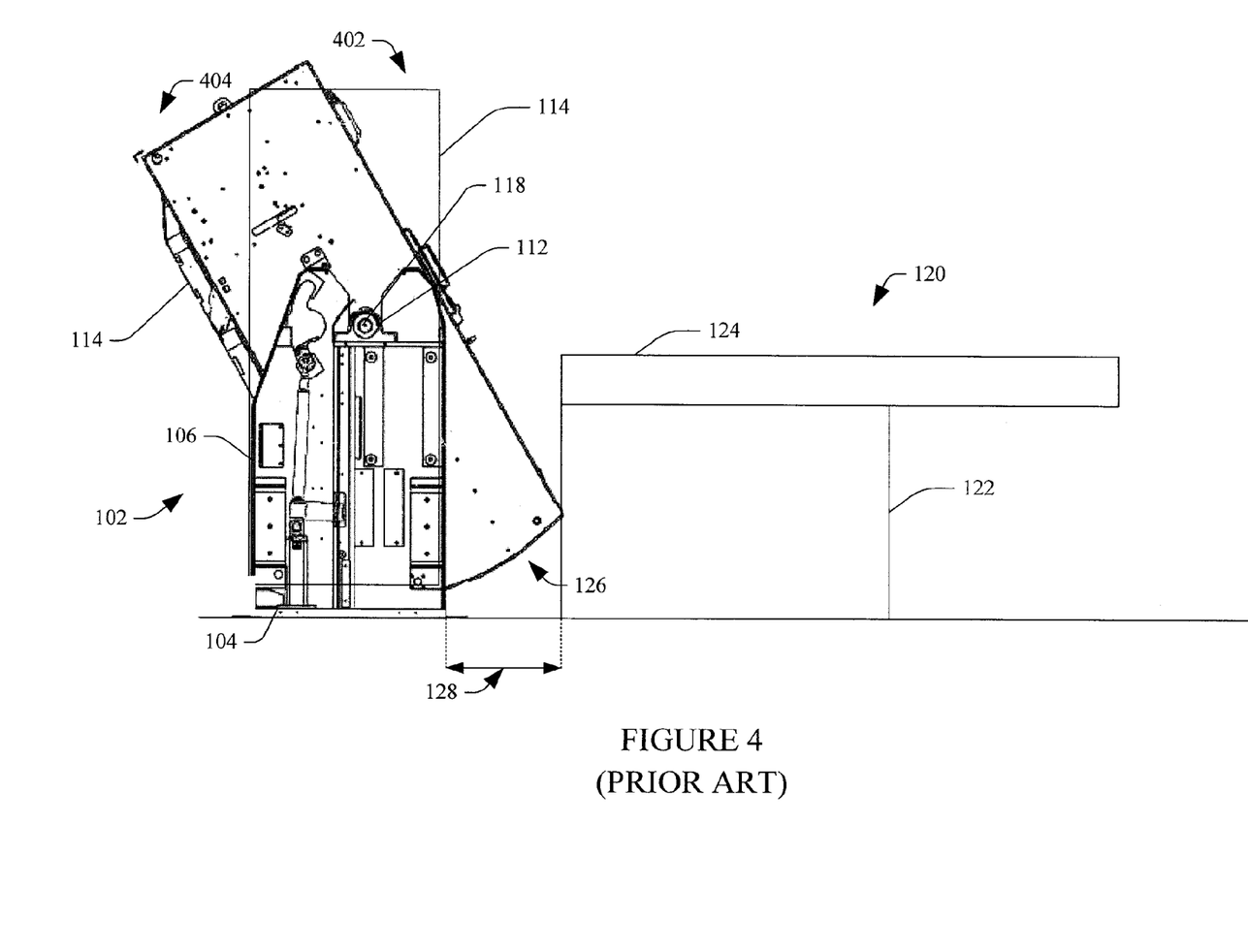

With respect to FIGS. 1 and 4, the tilt frame 114 is configured to tilt, about the tilt support 112 along a tilt axis 118, which extends transversely from side support 106 to side support 106 at about the center 110 or alternatively the center of gravity of the system (FIG. 1) of the examination region. Tilting the tilt frame 114 as such tilts the rotating gantry 101 about the tilt axis 118. The tilt frame 114 and the rotating gantry 101 can tilt from a vertical (or non-tilt) position 402 to a back (tilted) position 404 (as shown in FIG. 4) and/or a forward (tilted) position (not shown). When tilted in the back position 404, a bottom portion 126 (FIG. 4) of the tilt frame 114 protrudes out past the gantry base 104 by a distance 128 such that a support base 122 of a subject support 120 has to be located at least the distance 128 away from the gantry base 104 to avoid a collision with a tilted tilt frame 114.

With the scanner 100 of FIG. 1, the gantry base 104 and side supports 106 form a generally "U" shaped assembly (FIGS. 1 and 2), with a relatively large lateral width 130 (FIG. 2) and the side supports 106 running up past the center 110 of the examination region (FIG. 1) and connecting to the outside of the tilt frame 114 and the support frame 115 (FIG. 1). As a consequence, the gantry base 104 (FIGS. 1, 2 and 4) and the support frame 115 (FIGS. 1 and 3), and hence the system 100, tend to be relatively large, heavy, and/or expensive. A high compliance design will produce undesirably tight constraints on the allowable rotating gantry imbalance, while lower compliance can be achieved by higher frame stiffness and tighter tolerances between the frame interfaces, which increases cost. More specifically, the lateral stiffness of traditional tilt designs has always been a challenge, and the inherent large stiffness in and about all axes except the tilting generally is desirable. In addition, tight floor flatness tolerances over the large area of the gantry base 104 are needed to constrain the amount of load or distortion imposed on the base support.

Floor flatness tolerance may be reduced by adding significant structure between the tilt support locations, which can increase cost. Furthermore, the friction of the bearings of the tilt support 112 leads to wear and torque variance. Moreover, the scannable range of the subject support 120 is defined by the extent a table top 124 of the subject support 120 travels through the examination region. A consequence of tilting the tilt frame 114 about the tilt axis 118 is that the scannable range is decreased by the distance 128 as the support base 122 has to be at least the distance 128 away from the gantry base 104 as discussed above, or, in the alternative, the table top 124 (including the carriage system with guidance, bearing, motion devices, etc.) length has to be increased to compensate for the loss of the scannable distance 128, which can increase the cost of the subject support 120, Moreover, the base 104 and table top 124 (including the carriage, etc.) should be stiff enough to accommodate a large overhung load while keeping deflection within a predetermined tolerance.

SUMMARY OF THE INVENTION

Aspects of the present application address the above-referenced matters and others.

According to one aspect, an imaging system includes an annular shaped rotating gantry having an aperture and configured to support at least a radiation source, wherein the rotating gantry rotates about a rotation axis around an examination region, and wherein the rotation axis is located within the aperture in a center region of the examination region. The imaging system further includes a stationary gantry, configured to rotatably support the rotating gantry. The stationary gantry includes a gantry base, an annular shaped tilt frame that rotatably supports the rotating gantry, and a tilt system affixed to and between the gantry base and the tilt frame, wherein the tilt system defines a tilt axis of the stationary gantry, the tilt axis is located between the gantry base and the rotation axis, and the tilt frame tilts about the tilt axis.

According to another aspect, a method receiving a signal indicative of a tilt angle of a rotating gantry of an imaging system. The rotating gantry is annular shaped and has an aperture and rotates about a rotation axis located at a center region of the aperture. The method further includes actuating a tilt actuator of the imaging system to move a tilt frame of the imaging system in response to the signal. The tilt frame is affixed to a tilt support, and the rotating gantry is rotatably mounted to the tilt frame. Moving the tilt frame flexes the tilt support about a tilt axis of the tilt support, thereby tilting the tilt frame and the rotating gantry about the tilt axis, and the tilt axis is located below the rotation axis.

According to another aspect, a stationary gantry of an imaging system includes a base, a tilt frame, and at least two elastic members. The at least two elastic members are arranged at angles with respect to each other. Each of the at least two elastic members includes a first end affixed to the base and a second end affixed to the tilt frame. The least two elastic members define a tilt axis of the tilt frame at a crossing of the at least two elastic members. The tilt frame tilts about the tilt axis.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 5:
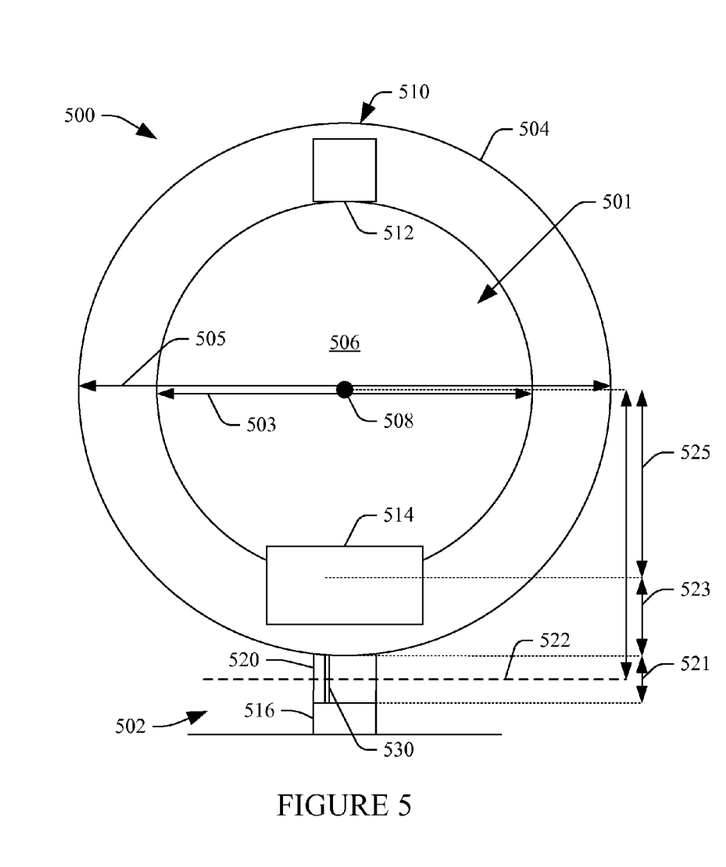
FIGS. 5, 6 and 7 schematically illustrate a tilt support of an imaging system.
Figure 6:
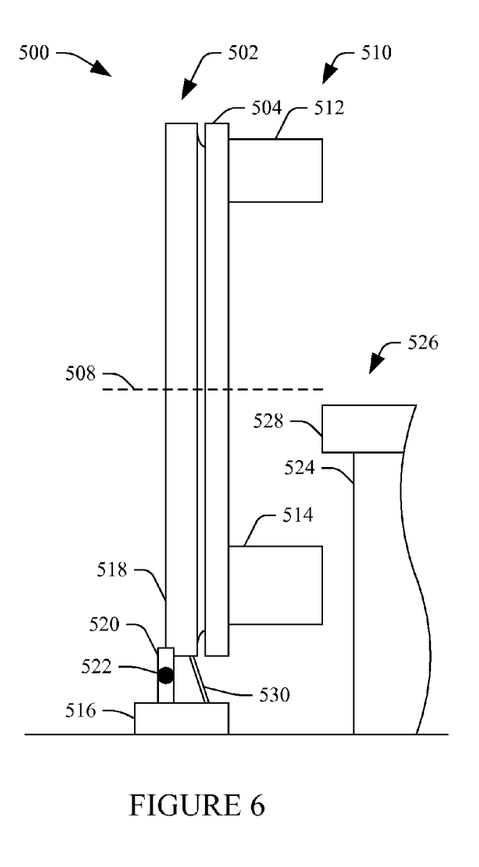
Figure 7:
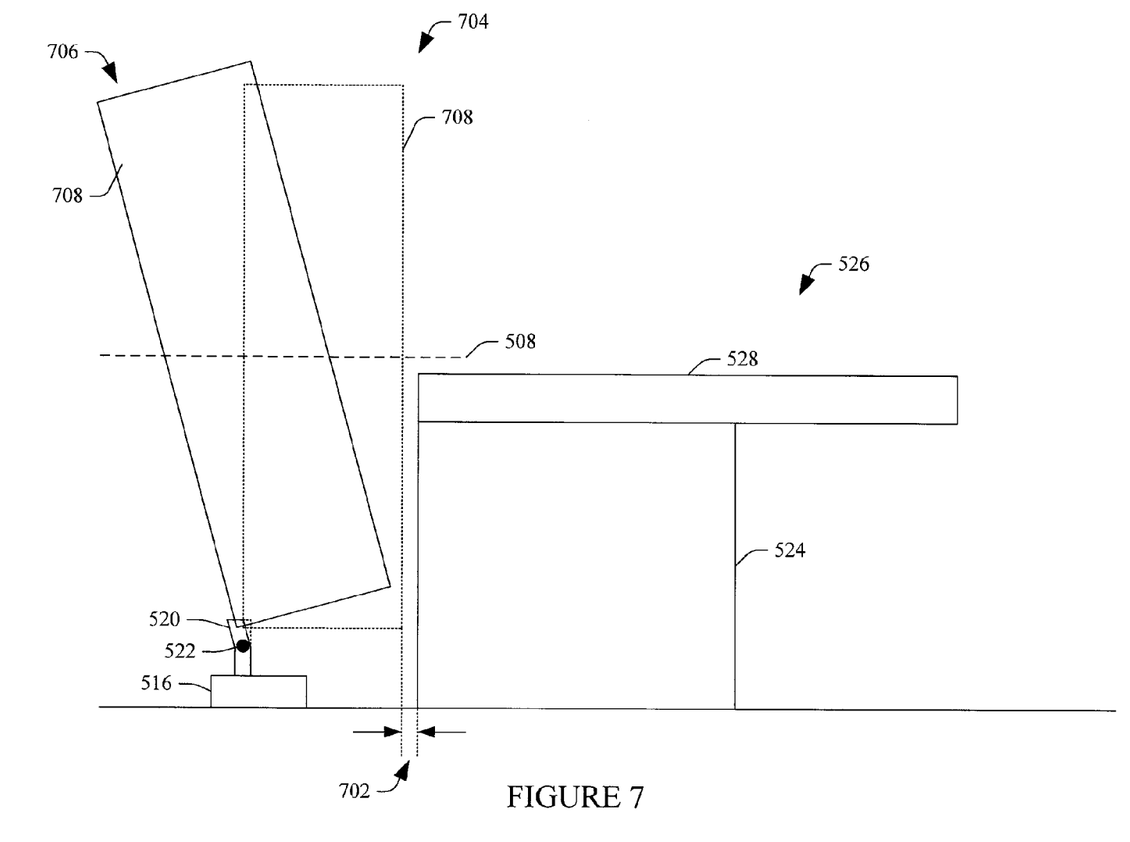

FIGS. 5, 6 and 7 schematically illustrate a portion of an imaging system 500, such as a computed tomography (CT) scanner. FIG. 5 schematically illustrates a front view and FIG. 6 schematically illustrates a side view, and FIG. 7 shows non-tilt and an example tilt position.

The imaging system 500 includes a generally stationary gantry 502 and a rotating gantry 504, which is rotatably supported by the stationary gantry 502 via a bearing or the like.

The rotating gantry 504 is annular (or ring shaped), having inner and outer diameters 503 and 505. The rotating gantry aperture 501 constrains the extent of an examination region. The rotating gantry 504 is configured to rotate around the examination region 506 about a rotation axis 508 (or iso-center), which is approximately at a center of the examination region 506. The rotating gantry portion 504 is configured to support various components 510 for generating, emitting and detecting radiation, and generating signals indicative of the detected radiation. In the illustrated embodiment, only a radiation source 512 and a radiation sensitive detector array 514 are shown for sake of clarity. However, other components which have been supported by the rotating gantry 504 include, but are not limited to, a heat exchanger, electrical cables, structural support members for supporting the components, balancing weights, etc. With a fourth generation system, the detector array 514 would instead be supported by the stationary gantry 502, The generally stationary gantry 502 includes a gantry base 516 configured to mount to an examination room floor, a tilt frame 518 (FIG. 6, and not visible in FIG. 5 in this example) configured to rotatably support the rotating gantry 504, and a tilt support 520 affixed between and to both the gantry base 516 and the tilt frame 518. The tilt frame 518, similar to the rotating gantry 504, is generally annular (or ring shaped), having an aperture that is larger than the aperture 501 of the rotating gantry 504 and with inner and outer diameters. The tilt support 520 defines a tilt axis 522, which the tilt frame 518 and hence the rotating gantry 504 tilts about. As shown, the tilt axis 522 is located below the axis of rotation 508, between the gantry base 514 and the axis of rotation 508.

Although the tilt axis 522 is shown at a height 521 between the gantry base 516 and the rotating gantry 504 in this embodiment, in other configurations, it may be at a height range 523 where it crosses the rotating gantry portion 504 and below the aperture 501, at a height range 525 where it crosses the aperture 501, but below the rotation axis 508, or at a height equal to or greater than the rotation axis 508. In addition, the illustrated tilt axis 522 is shown underneath the tilt frame 518. In other configurations, the tilt axis 522 can be otherwise located, for example, behind the tilt frame 518 (on the side of the tilt fram 518 facing away from the subject support 526), in front of the tilt frame 518 (on the side of the tilt frame 518 facing the subject support 526), partially under and to one of the sides, partially under and to both sides, or not under and to both sides.

With the location of the tilt axis 522 below the rotation axis 508, the size of the generally stationary gantry 502 can be smaller than a configuration in which the tilt axis is as high or higher than the rotation axis 508 (e.g., as shown in FIG. 1). For example, in FIGS. 5, 6 and 7, the tilt support 520 does not extend up to the height of the rotation axis 508 as does the configuration shown in FIG. 1, and the gantry base 516 and tilt support 520 are smaller and weigh less than that shown in FIGS. 1-4. Furthermore, with this tilt axis 522 below the tilt frame 518, the tilt support, relative to the tilt support 115 of FIG. 3, can be smaller. Generally, the reduction in size and/or weight of the base 516 and the tilt support can be up to 75%, relative to the configuration shown in FIGS. 1-4, for example, 20%, 30%, 45%, 50%, or another percent up to 75% or higher, which not only reduces the foot print and weight of the system 500, but also may reduce the overall cost of the system 500.

Moreover, with the lower tilt axis 522, a support base 524 of a subject support 526, which supports an object or subject in the examination region 506 before, during and/or after scanning, can be located closer to the rotating gantry 504 without a collision between a tilted rotating gantry 504 and the support base 524, relative to the configuration in FIGS. 1-4, as shown in FIG. 7, by a distance 702 that is suitable for both a non-tilt position 704 and a tilt position 706 of the tilt frame 518 and the rotating gantry 504 (collectively shown as 708 for clarity purposes in this example). Thus, for a given longitudinal length of a table top 528, the untilted scannable range, is larger, relative to the configuration shown in FIG. 4. As such, the scannable range can be extended for the system 500, cost can be reduced by decreasing the length of the table top 528 for a given scannable range, or a combination of extended scannable range and table top 528 cost reduction and/or performance improvement can be achieved.

With reference to FIGS. 5, 6 and 7, a tilt actuator 530 (FIGS. 5 and 6) is configured to move the tilt frame 518 between tilt position 706 (FIG. 7) and the non-tilt position 704 (FIG. 7). Examples of suitable actuators include a piston with linear ball screw, a hydraulic piston, and/or other tilt actuator. One or more springs or the like may be used to assist the actuator 530. In the illustrated embodiment, only a single tilt actuator 530 is shown. However, more than one similar or different tilt actuator 530 can be used. Furthermore, the location of the illustrated tilt actuator 530 is not limiting, and the tilt actuator 530 can be located in front of the tilt support 520 (as shown), behind that tilt support 520, to a side of the tilt support 520, and/or otherwise located. An optional brake(s) (not shown) can be used along with the tilt actuator 530.

In one instance, the tilt actuator 530 is used to tilt a normally non-tilted tilt frame 518 to a tilt position (e.g., from zero (0) degrees to thirty (30) degrees). In another instance, the tilt actuator 530 is used to move a normally tilted tilt frame 518 to a non-tilted position (e.g., from 30 degrees to 0 degrees). In yet another instance, the tilt actuator 530 is used to move a normally tilted tilt frame 518 between a further tilted and a non-tilted position (e.g., from fifteen (15) degrees to 30 degrees or 0 degrees, from 0 degrees to negative thirty (−30) degrees or to positive thirty (+30) degrees, etc.). With the foregoing, 0 degrees represents the vertical position such as the position at 704 (FIG. 7) and 30 degrees represents either a back tilt (FIG. 7) or a forward tilt (not shown). However, it is to be understood that these tilt angles are relative angles and the particular angle values of 0, 15, and 30 are for explanatory purposes and are not limiting. In addition, the above tilt ranges of 30 and 60 degrees are also for explanatory purposes and are not limiting A tilt actuator controller (not visible) is configured to actuate the tilt actuator 530. For example, in response to a console of the imaging system 500 receiving an input indicative of a scan protocol that includes a non-zero (with respect to the vertical) tilt angle of the rotating gantry 504, the console sends an instruction to the controller, and the controller actuates the tilt actuator 530 to tilt the tilt frame 518 based on the tilt angle. After the scan, the console can send an instruction to the controller, and the controller actuates the tilt actuator 530 to return the tilt frame 518 to the vertical position or move the tilt frame 518 to another tilt angle. The input signal may be in response to a user selecting a protocol via a mouse, a keyboard, or other input device, and/or otherwise, the user selecting or indicating a specific tilt angle, and/or otherwise. In yet another embodiment, controls located on the stationary gantry or elsewhere allow the user to manually tilt the tilt frame 518. The user can be an authorized imaging technician or clinician, service personnel, manufacturing personnel, and/or other authorized person or robot.

Other components generally utilized with the system 500, but are not shown for sake of brevity and clarity, include a reconstructor that reconstructs the signals generated by the detector array 512 to generate volumetric image data and an operator console (e.g., a general purpose or dedicated computer) with software resident thereon that allows an operator to control an operation of the system 100, for example, to select tilt and non-tilt protocols, manually tilt the tilt frame 518, initiate scanning, etc.

It is to be understood that the relative geometry and/or location of one or more of the components 500, 502, 504, 512, 514, 516, 518 and 520 are provided for explanatory purposes and are not limiting. As such, in other embodiments, one or more of these components can have other relative geometry and/or be otherwise located.

Figure 8:
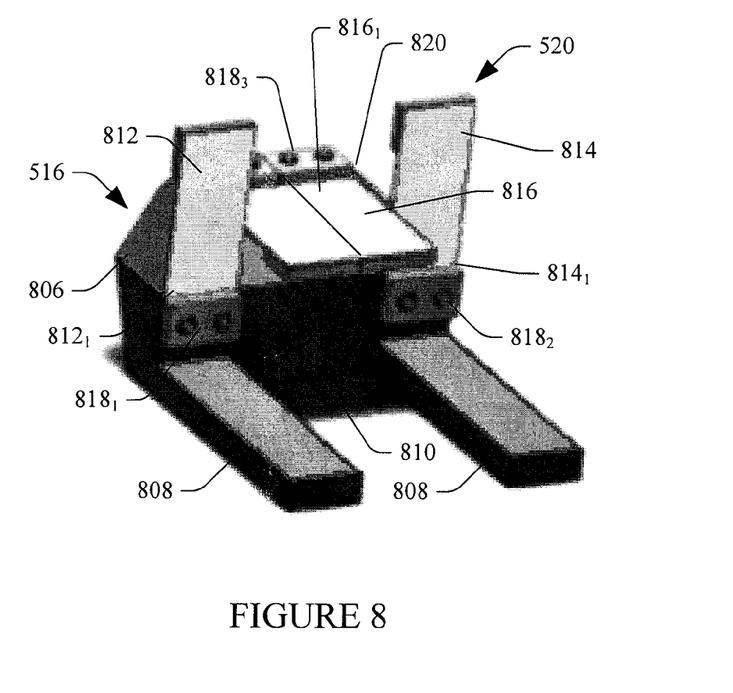
FIGS. 8, 9 and 10 illustrate an example of the tilt support of FIGS. 5, 6 and 7.
Figure 9:
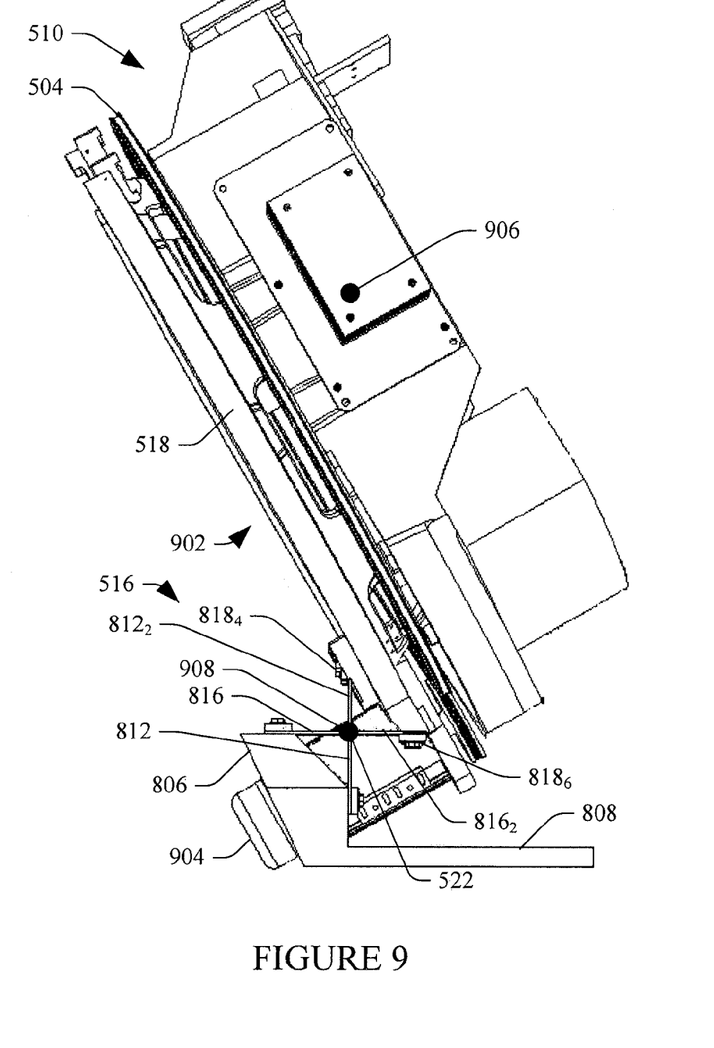
Figure 10:
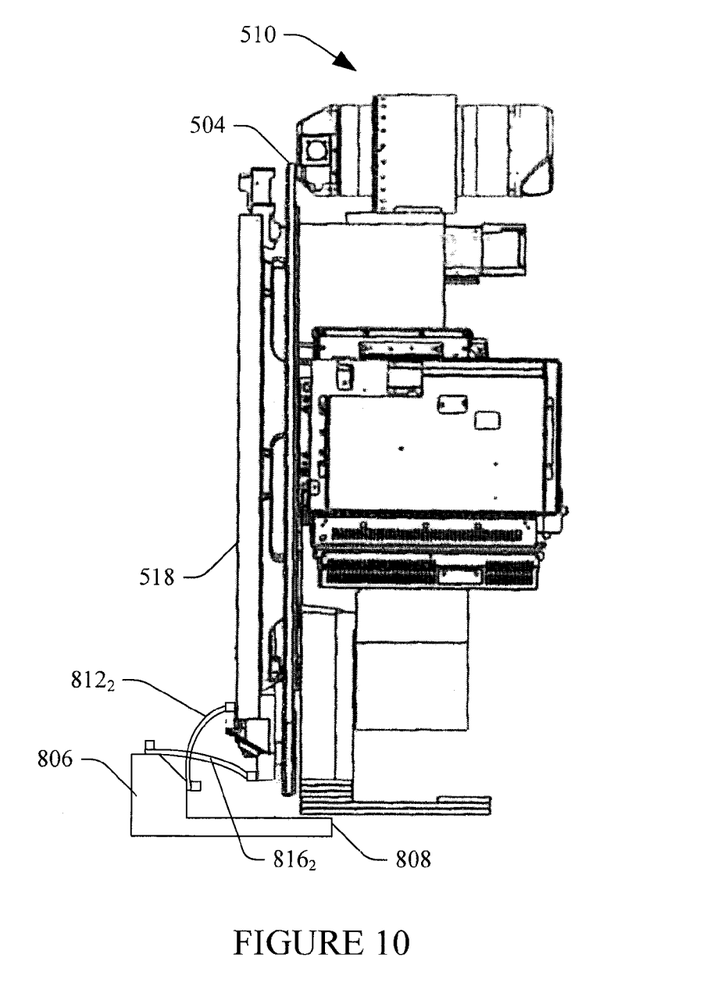
Figure 11:
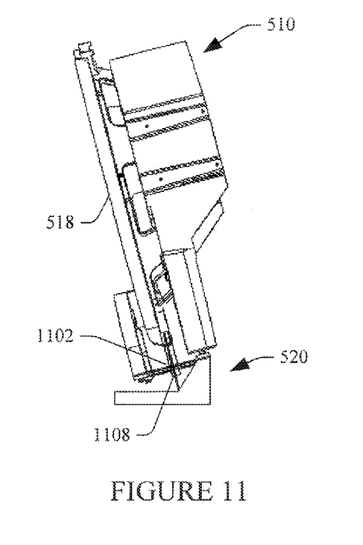
FIGS. 11, 12, 13 and 14 illustrate another example of the tilt support of FIGS. 5, 6 and 7.
Figure 12:
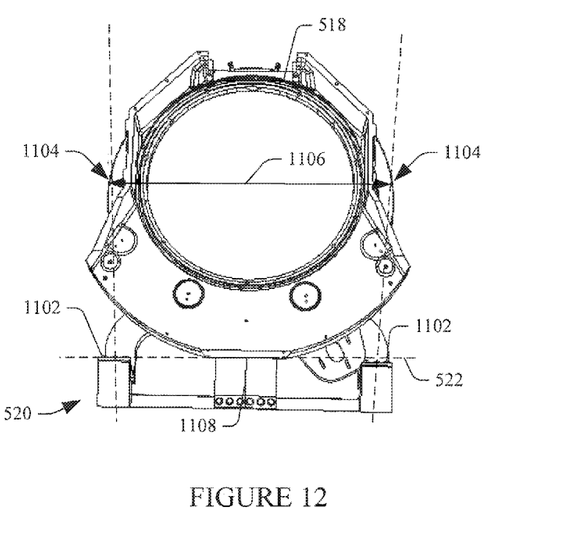
Figure 13:
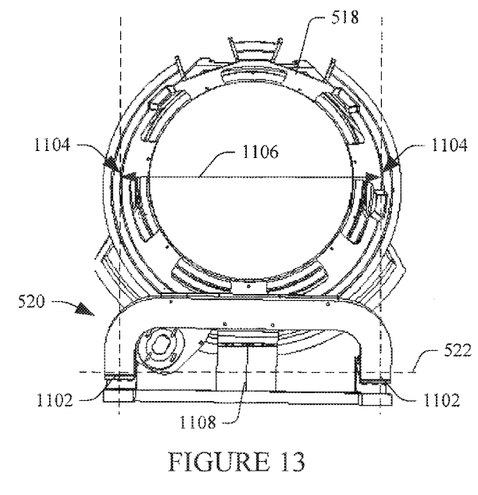
Figure 14:
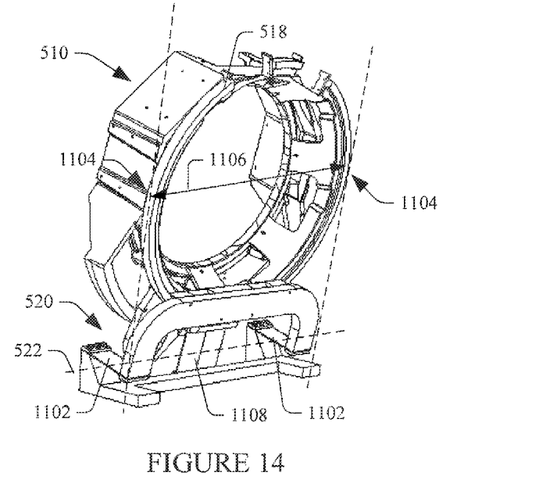

FIGS. 8, 9 and 10 illustrate an example of the tilt support of FIGS. 5, 6 and 7. FIG. 8 illustrates a non-limiting embodiment of the tilt support 520 in connection with the gantry base 516, FIG. 9 illustrates the non-limiting tilt support 520 of FIG. 8 in connection with the gantry base 516, the tilt frame 518, the rotating gantry portion 504, and some of the components 510 attached to the rotating gantry portion 504, where the normal state of the tilt frame 518 is a tilted state, and FIG. 10 illustrates FIG. 9 where the actuator 530 is to used move the tilt frame 518 to the vertical non-tilted position. Note that the tilt actuator 530 is not shown in these figures.

Initially referring to FIG. 8, with this embodiment, the base 516 includes a body 806 and at least one leg 808 (two legs 808 shown in the illustrated embodiment). The legs 808 protrude essentially horizontally and in a similar direction from a same side 810 of the body 806. Generally, when installed within the system 500, the side 810 of the body 806 faces the subject support 526 (FIGS. 6 and 7). The tilt support 520 includes at least one elastic member such as a leaf spring, a coil spring, and/or other elastic member. For explanatory purposes, the following is described in the context of a leaf spring. However, it is to be understood that other elastic members are contemplated herein.

As shown, the tilt support 520 includes a first leaf spring 812, a second leaf spring 814 and a third leaf spring 816. First end regions $812_1$ and $814_1$ of the first and second leaf springs 812 and 814 are fastened via fasteners $818_1$ and $818_2$ to the side 810 of the body 806, separated by a non material region, and symmetrically extend vertically upward with respect to the legs 808. In other embodiments, the leaf springs 812 and 814 do not extend symmetrically. In addition, the illustrated leaf springs 812 and 814 are the same length, however, the leaf springs 812 and 814 can be different lengths. A first end region $816_1$ of the third leaf spring 816 is fastened via a fastener $818_3$ to a top 820 of the body 806 and extends parallel to the legs 808 and between the non material region between the first and second leaf springs 812 and 814. The leaf spring 816 can be the same or different length as at least one of the leaf springs 812 or 814.

Turning to FIG. 9, when installed with the tilt frame 518, second end regions $812_2$ and $814_2$ (not visible) of the first and second leaf springs 812 and 814 (not visible) are fastened via fasteners $818_4$ and $818_5$ (not visible) to a backside 902 of the tilt frame 518, which faces away from the rotating gantry portion 504. Furthermore, second end region $816_2$ of the third leaf spring 816 is fastened via a fastener $818_6$ also to the backside 902 of the tilt frame 518. In FIG. 9, a motor 904 that rotates the rotating gantry portion 504 via a belt, a chain, a gear, or the like is also shown.

In the embodiment shown in FIG. 9, the tilt frame 518 is mounted to the tilt support 516 such that the (vertical) leaf springs 812 and 814 and the (horizontal) leaf spring 816 are perpendicular to each other and unflexed, with the tilt axis 522 located an intersection 908 of the springs 812 and 814 with the spring 816. In the illustrated embodiment, the intersection is located at one half of the lengths of the leaf springs 812 and 814 and one half of the length the leaf spring 816. The tilt axis 522 is located at the intersection 908, which, in this embodiment, is located in behind the tilt frame 518 (on the side of the tilt frame 518 opposite to the side facing the subject support 526). In other embodiments, the intersection 908 and/or tilt axis 522 are otherwise located, as described herein.

The illustrated tilt frame 518 is tilted at an angle with respect to the vertical. Suitable angles include an angle between zero (vertical) and forty-five (45) degrees, such as thirty (30) degrees, fifteen (15) degrees, or other angle. An angle between full tilt and no tilt (e.g., 15 degrees where tilting between 0 and 30 degrees) may reduce tilt motor power requirements. In the illustrated embodiment, the frame 518 is tilted such that a center of gravity 906 of the combination of the rotating gantry portion 504 and the components 510 is located above the intersection 908 of the leaf springs 812 and 814 and the leaf spring 816. However, in other embodiments, the center of gravity 906 can be in front of or behind the tilt axis 522. In one instance, offsetting the center of gravity 906 adds preload to the actuator, which may be beneficial when the actuator system has backlash (i.e., a very low stiffness region going from compression to tension). Preload can be used to compensate for the imbalanced rotor loads.

With this embodiment, when tilted forward (as shown in FIG. 10) or further backward (not shown), the leaf springs 812, 814 and 816 flex and force thereto naturally counters the tilt moment load. This allows for a lower stroke and low load tilt actuator, relative to a configuration without the leaf springs 812-816 (e.g., FIGS. 1-4), which may also reduce overall cost. Furthermore, equipment safety can be improved by lowering loads of individual components. By way of non-limiting example, it is possible to have a failure in one component and the equipment still have complete functionality. By way of another non-limiting example, the lower power actuator mitigates harm to the scanned object.

By using the two vertical leaf springs 812 and 814 spaced apart, stiffness can be increased and twisting about the leaf springs can be mitigate relative to a configuration in which only a single vertical leaf spring is used. In other embodiments, more than two vertical and/or horizontal leaf springs and/or less than two vertical and/or horizontal leaf springs can be utilized.

Variations are contemplated.

In FIG. 9, the leaf springs 812, 814, 816 are in an unflexed state when the tilt frame 518 is tilted. In one variation, at least one of the two leaf springs 812 and 814 or the leaf spring 816 can be alternatively configured so as to be in a flexed state when the tilt frame 518 is tilted.

In FIG. 10, the leaf springs 812, 814, 816 are in a flexed state when the tilt frame 518 is in a non-tilted vertical position. In a variation, at least one of the two leaf springs 812 and 814 or the leaf spring 816 can be alternatively be configured so as to be in an unflexed state when the tilt frame 518 is in the non-tilted vertical position.

In another variation, the two vertical leaf springs 812 and 814 can be configured alternatively as horizontal leaf springs, and the one horizontal leaf spring 816 can be configured alternatively as one or more vertical leaf springs.

In another variation, a single vertical leaf spring (either leaf spring 812 or 814) is used and the other leaf spring is omitted. Omitting one of the leaf springs 812 or 814 further reduces the overall size and/or cost of the tilt system 516. However, using both of the vertical leaf springs 812 and 814 may reduce twisting about the longitudinal axes of the leaf springs 812 and 814 relative to a configuration with a single vertical leaf spring.

In another variation, the tilt support 516 includes more than two vertical leaf springs 812 and 814 and/or more than one horizontal leaf spring 816.

In another variation, at least two of the two vertical leaf springs 812 or 814 and/or the horizontal leaf spring 816 are configured as a single leaf spring.

Generally, the configuration of the tilt support 216 shown in FIGS. 8-10 results in an optimally small frame size.

FIGS. 11, 12, 13 and 14 illustrate a non-limiting configuration of the tilt support 520. As shown in these figures, outer leaf springs 1102 are spaced further apart that the outer leaf springs 812 and 814 in FIGS. 8-10. More particularly, the leaf springs 1102 respectively are located approximately below outer edges 1104 of an outer diameter 1106 of the tilt frame 518. As a result, the tilt support 520 in FIGS. 11-14 is stiffer and less susceptible to twisting relative to the configuration shown in FIGS. 8-10. With this configuration, the tilt axis 522 is located in behind the tilt frame 518 (on the side of the tilt frame 518 opposite to the side facing the subject support 526) and below the tilt frame 518, the rotating gantry 504, and the components 510 thereon. In addition, the outer leaf springs 1102 are angled horizontal leaf springs, and inner leaf springs 1108 are angled vertical leaf springs. When optimized for stress, the leaf springs are undeflected at the center of the tilting range.

Figure 15:
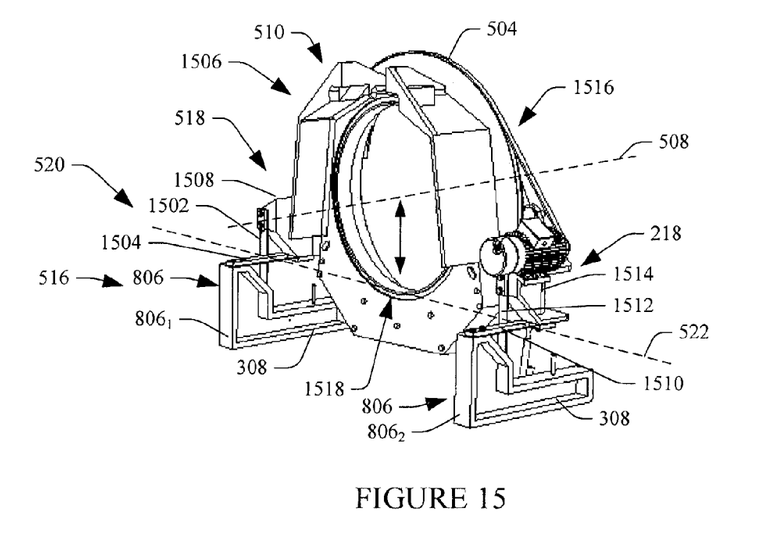
FIGS. 15 and 16 illustrate another example of the tilt support of FIGS. 5, 6 and 7.
Figure 16:
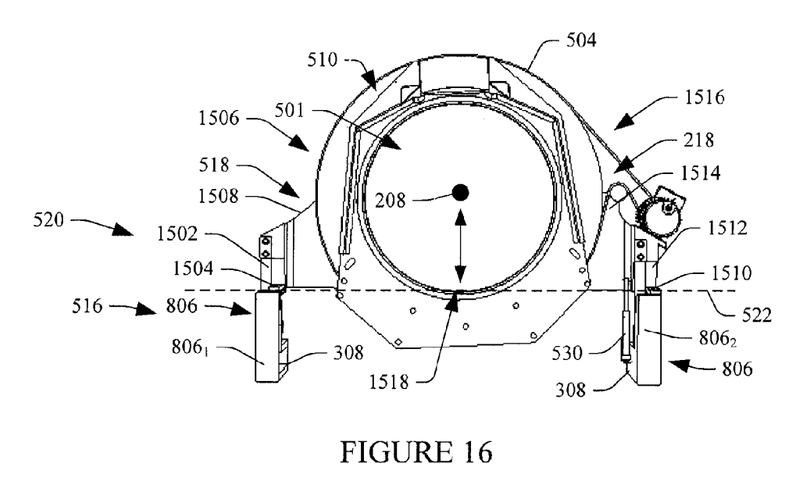

FIGS. 15 and 16 illustrate another non-limiting variation of the tilt support 520. With this configuration, outer leaf spring 1502 and inner leaf spring 1504 are located to the left of one side 1506 of the rotating gantry portion 504 and affixed to a first side region 1508 of the tilt frame 518, which protrudes to the left past the outer diameter of the rotating gantry portion 504. Similarly, outer leaf spring 1510 and inner leaf spring 1512 are located to the right of a second opposing side 1514, which is across the examination region from the first side 1506, of the rotating gantry 504 and affixed to a second side region 1516 of the tilt frame 518, which protrudes to the right past the outer diameter of the rotating gantry portion 504.

The body 806 of the base 516 includes first and second body halves $806_1$ and $806_1$, each with one of the legs 808, which faces in a direction away from the subject support 526 (FIGS. 6 and 7). The outer leaf spring 1502 is mounted horizontally between the first body half $806_1$ and the tilt frame 518, and the inner leaf spring 1504 is mounted vertically between the first body half $806_1$ and the tilt frame 518. In contrast, the outer leaf spring 1510 is mounted vertically between the second body half $806_2$ and the tilt frame 518, and the inner leaf spring 1512 is mounted horizontally between the second body half $606_2$ and the tilt frame 518.

In this embodiment, the tilt actuator 530 is located in connection with one of the legs 808. In addition, the tilt axis 522 is located in front of the tilt frame 518 (between the tilt frame 518 and the subject support 526) and below the axis of rotation 508 and crosses at about a perimeter 1518 of the aperture 501 of the rotating gantry 504. In another instance, the tilt axis is below or above the perimeter 1518 of the aperture 501.

Figure 17:
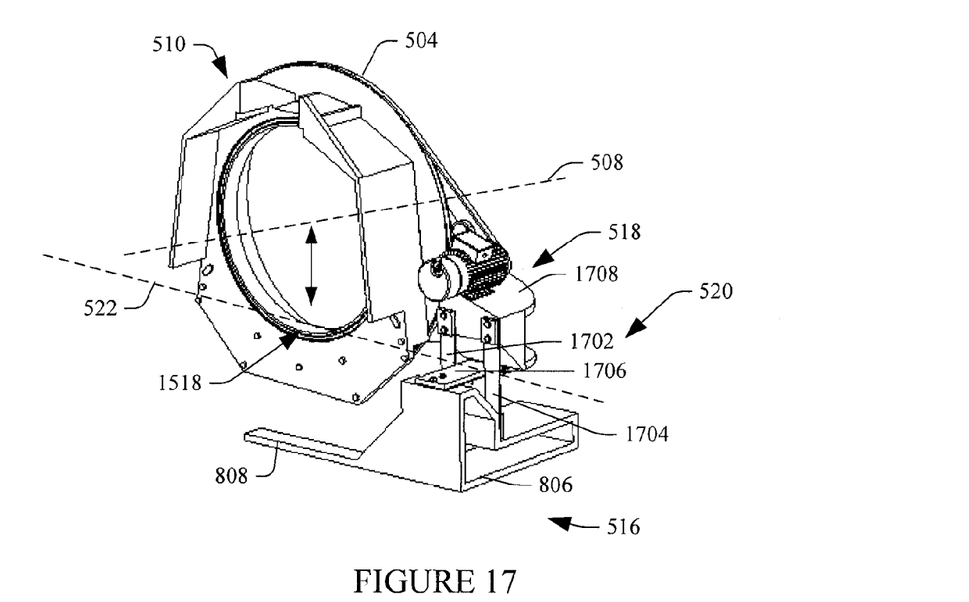
FIGS. 17 and 18 illustrate another example of the tilt support of FIGS. 5, 6 and 7.
Figure 18:
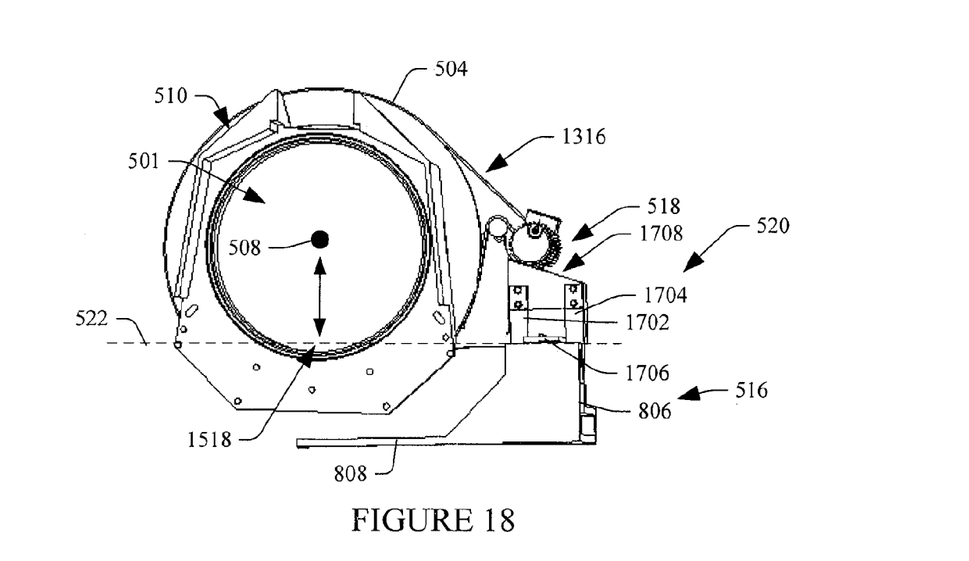

FIGS. 17 and 18 illustrate another non-limiting variation of the tilt support 220. With this configuration, all of leaf springs 1702, 1704 and 1706 are located to one side of the rotating gantry 504 and affixed to a side region 1708 of the tilt frame 518 which protrudes out past the outer diameter of the rotating gantry 504. The base 516 includes the body 806, which, in this example, has a single leg 808, which faces in a direction perpendicular to the subject support 526 (FIGS. 6 and 7) along a transverse axis of the system 500.

The leaf springs 1702 and 1704 are mounted vertically between the body 806 and the side region 1708 and spaced apart by a non-material region. The leaf spring 1706 is mounted horizontally between the body 806 and the side region 1708, perpendicular to and in between the leaf springs 1702 and 1704. The tilt axis 522 is located in front of the tilt frame 518 (between the tilt frame 518 and the subject support 526) and below the axis of rotation 508, and crosses just above the perimeter 1518 of the aperture 501 of the rotating gantry 504. In another instance, the tilt axis is at or below the perimeter 1518 of the aperture 501.

In another variation, at least one of the leaf springs described herein includes one or more additional leaf springs stacked adjacent thereto. With this configuration, the additional leaf springs are fixidly mounted via one end and include a free floating end, which is free to translate with respect to the fixed end as the one or more of the leaf springs flex.

In another variation, the gantry base 516 is part of the subject support base 524.

The tilt system 520 may also be used to employ the system 500 as a service tool to lift and/or set down components, for example, since the natural motion of tilt will move the rotor near vertical at the six o' clock rotor location.

Figure 19:
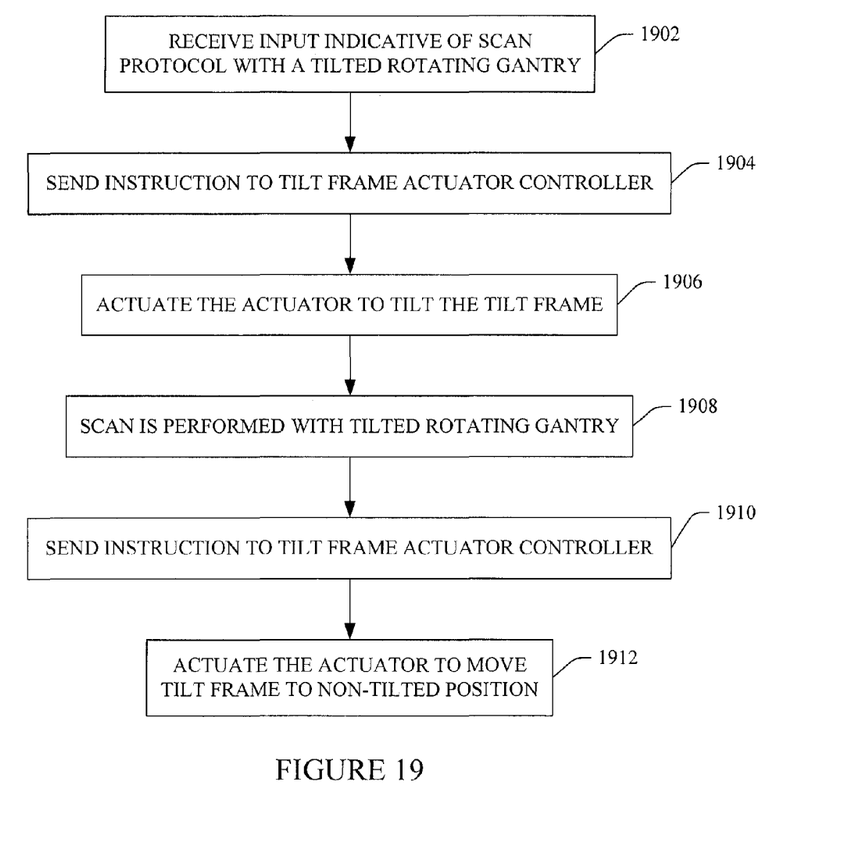
FIG. 19 illustrates an example method.

FIG. 19 illustrates an example method.

It is to be appreciated that the ordering of the acts in the methods described herein is not limiting. As such, other orderings are contemplated herein. In addition, one or more acts may be omitted and/or one or more additional acts may be included.

At 1902, a console of the imaging system 500 receives a signal indicative of a scan protocol, which includes a non-zero (with respect to the vertical) tilt angle of the rotating gantry 504. The signal may be in response to a user selecting a protocol via a mouse, a keyboard, or other input device, and/or otherwise.

At 1904, the console sends an instruction to the controller 529 that controls the tilt actuator 530. The instruction includes the non-zero tilt angle.

At 1906, the controller actuates the tilt actuator 530 to tilt the tilt frame 518 based on the tilt angle.

At 1908, the scan is performed with the tilted rotating gantry 504.

At 1910, the console sends another instruction to the controller 529 that controls the tilt actuator 530.

At 1912, the controller actuates the tilt actuator 530 to return the tilt frame 518 to its home position.

The above may be implemented by way of computer readable instructions, which when executed by a computer processor(s), cause the processor(s) to carry out the described acts. In such a case, the instructions are stored in a computer readable storage medium associated with or otherwise accessible to the relevant computer.

The following provides a non-limiting example for determining suitable leaf springs. For this example, the lowered tilt location provides a spring compensation for a tilt moment that varies from 0 to 1000 nm in 30 degrees. The stiffness for an orientation of two perpendicularly arranged leaf springs with intersection at ½ l can be determined through: stiffness=2EI/l, where a max stress=φEt/(2 l), E=Leaf Spring Modulus of Elasticity, l=leaf spring length, I=leaf spring inertia, t=leaf spring thickness, and f=leaf spring angle. The rotational stiffness can be determined through: K=Mmax/φ, where K=954.93 Nm/rad. With steel with a modulus of: E=2.1E11 Pa, a length of: l=0.2 m, and a width of: b=0.250 m, the thickness of the spring can be determined through:

$$t = \sqrt[3]{\frac{12Kl}{2Eb}},$$

where t=3.521×10⁻³ m. The stress of the cross flexure is dominated by bending can be determined through:

$$\sigma = \frac{\phi E t}{2l},$$

where σ=9.679×10⁸ N/m².

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

The invention claimed is:

1. An imaging system, comprising:
   an annular shaped rotating gantry having an aperture and configured to support at least an X-ray radiation source, wherein the rotating gantry rotates about a rotation axis around an examination region, and wherein the rotation axis is located within the aperture in a center region of the examination region; and
   a stationary gantry, configured to rotatably support the rotating gantry, the stationary gantry, including:
      a gantry base;
      an annular shaped tilt frame that rotatably supports the rotating gantry; and
      a tilt system fastened to and between the gantry base and the tilt frame with non-bearing fasteners, wherein the tilt system defines a tilt axis of the stationary gantry, the tilt axis is located between the gantry base and the rotation axis, and the tilt frame tilts about the tilt axis.

2. The imaging system of claim 1, wherein the tilt axis is at about or below the aperture.

3. The imaging system of claim 1, wherein the tilt system is rigidly fastened to the gantry base and to the tilt frame using the non-bearing fasteners which include at least one of a latch, a screw, a bolt, a buckle, a button, a catch, a clasp, a lock, a rivet or a snap.

4. The imaging system of claim 1, wherein the tilt axis is below the tilt frame.

5. The imaging system of claim 4, wherein the tilt system is located below the aperture.

6. The imaging system of claim 5, wherein the tilt system includes an actuator which includes at least one of a piston with a linear ball screw or a hydraulic piston.

7. The imaging system of claim 6, wherein the tilt system is located in a region within an outer diameter of the tilt frame.

8. The imaging system of claim 1, the tilt system, comprising:
   at least one elastic member having a first end fastened to the gantry base and a second opposing end fastened to the tilt frame, wherein the at least one elastic member transitions between flexed and unflexed states in response to moving the tilt frame between a vertical non-tilted position and a tilted position or the tilted position and the vertical non-tilted position.

9. The imaging system of claim 8, wherein the at least one elastic member includes at least two elastic members arranged at perpendicular angles with respect to each other, wherein the tilt axis extends along an intersection of a crossing of the at least two elastic members, and at least one of the two elastic members arranged parallel to the rotation axis.

10. The imaging system of claim 9, wherein the at least two elastic members intersect at approximately half a length of a first of the at least two members and at approximately half a length of a second of the at least two members.

11. The imaging system of claim 9, wherein one of the at least two members extends vertically and another of the at least two members extends horizontally.

12. The imaging system of claim 9, wherein one of the at least two members extends vertically at a non-zero from the vertical and another of the at least two members extends horizontally at a non-zero angle from the horizontal.

13. The imaging system of claim 8, wherein the at least one elastic member includes at least one of a leaf spring or a coil spring.

14. The imaging system of claim 8, wherein the at least one elastic member, when flexed, counters the tilt moment load.

15. A method, comprising:
receiving a signal indicative of a tilt angle of a rotating gantry of an imaging system, wherein the rotating gantry is annularly shaped and has an aperture and rotates about a rotation axis located at a center region of the aperture; and
actuating a tilt actuator of the imaging system to move a tilt frame of the imaging system in response to the signal,
wherein the tilt frame is fastened to a tilt support using non-bearing fasteners, and the rotating gantry is rotatably mounted to the tilt frame, and
wherein moving the tilt frame flexes the tilt support about a tilt axis of the tilt support, thereby tilting the tilt frame and the rotating gantry about the tilt axis, and the tilt axis is located below the rotation axis.

16. The method of claim 15, wherein the tilt axis is located below the aperture of the tilt frame.

17. The method of claim 16, wherein the tilt axis is located below the tilt frame.

18. The method of claim 15, wherein the tilt support flexes between non-flexed and flexed states in response to moving the tilt frame, and the tilt support is fastened to the tilt frame with fasteners.

19. The method of claim 15, wherein moving the tilt frame from a vertically non-tilted position to a tilted position transitions the tilt support to a flexed state; moving the tilt frame from a tilted position to a vertically non-tilted position transitions the tilt support to a flexed state; moving the tilt frame from a vertically non-tilted position to a tilted position transitions the tilt support to an unflexed state, or moving the tilt frame from a tilted position to a vertically non-tilted position transitions the tilt support to an unflexed state.

20. The method of claim 15, wherein the tilt actuator includes at least one of a piston with a linear ball screw or a hydraulic piston.

21. The method of claim 15, wherein the tilt axis is located in front of the tilt frame; behind the tilt frame, or below the tilt frame.

22. A stationary gantry of an imaging system, comprising:
a base;
a tilt frame; and
at least two elastic members arranged at angles with respect to each other, wherein each of the at least two elastic members includes a first end affixed to the base and a second end affixed to the tilt frame, and wherein the least two elastic members define a tilt axis of the tilt frame at a crossing of the least two elastic members, wherein the tilt frame tilts about the tilt axis.

23. The stationary gantry of claim 22, wherein at least one of the at least two elastic members is a leaf spring.

* * * * *